:(12) United States Patent
Noguchi et al.

(10) Patent No.: US 9,006,671 B2
(45) Date of Patent: Apr. 14, 2015

(54) RADIOLOGICAL IMAGE DETECTION APPARATUS

(75) Inventors: Shinsuke Noguchi, Kanagawa (JP); Akihito Bettouyashiki, Kanagawa (JP); Makoto Sugizaki, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 300 days.

(21) Appl. No.: 13/600,561

(22) Filed: Aug. 31, 2012

(65) Prior Publication Data

US 2013/0077762 A1    Mar. 28, 2013

(30) Foreign Application Priority Data

Sep. 28, 2011  (JP) .................................. 2011-213317

(51) Int. Cl.
*G03B 42/04* (2006.01)
*A61B 6/00* (2006.01)

(52) U.S. Cl.
CPC .............. *G03B 42/04* (2013.01); *A61B 6/4405* (2013.01)

(58) Field of Classification Search
CPC .... G03B 42/04; A61B 6/4216; A61B 6/4283; A61B 6/4291; A61B 6/4405; A61B 6/00; A61B 6/4233; A61B 6/4266; A61B 6/4452; A61B 6/46; A61B 6/5235; G01T 1/2018
USPC ......... 250/370.8, 370.9, 336.1, 580; 378/189, 378/62, 98
See application file for complete search history.

(56) References Cited

U.S. PATENT DOCUMENTS

| | | | |
|---|---|---|---|
| 6,287,140 | B1 | 9/2001 | Itoh |
| 6,933,655 | B2 * | 8/2005 | Morrison et al. ............. 310/314 |
| 7,767,981 | B2 * | 8/2010 | Kuwabara et al. ......... 250/484.4 |
| 7,952,080 | B2 * | 5/2011 | Kuwabara et al. ......... 250/484.4 |
| 2006/0054822 | A1 * | 3/2006 | Tsuchino ................... 250/336.1 |
| 2008/0054182 | A1 * | 3/2008 | Yokoyama et al. ...... 250/370.09 |

(Continued)

FOREIGN PATENT DOCUMENTS

| | | |
|---|---|---|
| JP | 10-275605 A | 10/1998 |
| JP | 2000-163161 A | 6/2000 |

(Continued)

OTHER PUBLICATIONS

Japanese Office Action Issued in JP 2011-213317 on Dec. 11, 2013.

(Continued)

*Primary Examiner* — David A Vanore
(74) *Attorney, Agent, or Firm* — Jean C. Edwards, Esq.; Edwards Neils PLLC

(57) ABSTRACT

A radiological image detection apparatus includes: a lock mechanism including at least one first lock mechanism and at least one second lock mechanism, each including a coupling member moving between a coupling position at which the lock mechanism is coupled to a battery and a non-coupling position, the coupling member being installed with a manipulation part exposed to an outer surface of a portion of a case in which a battery accommodating part is installed, and the first lock mechanism setting a first direction of a movement direction of the corresponding coupling member from the coupling position to the non-coupling position and the second lock mechanism setting a second direction of a movement direction of the corresponding coupling member from the coupling position to the non-coupling position, being different from the first direction.

11 Claims, 16 Drawing Sheets

(56) References Cited

U.S. PATENT DOCUMENTS

| | | |
|---|---|---|
| 2008/0118034 A1 | 5/2008 | Aoyagi |
| 2009/0032737 A1 | 2/2009 | Kuwabara et al. |
| 2010/0230606 A1* | 9/2010 | Liu et al. ............... 250/370.04 |
| 2010/0259409 A1* | 10/2010 | Kuwabara et al. ......... 340/815.4 |
| 2012/0069966 A1* | 3/2012 | Kobayashi .................. 378/189 |
| 2012/0161026 A1* | 6/2012 | Kitano et al. ............... 250/394 |
| 2013/0077762 A1* | 3/2013 | Noguchi et al. ............. 378/189 |
| 2014/0016747 A1* | 1/2014 | Watanabe ..................... 378/62 |
| 2014/0093040 A1* | 4/2014 | Omura ......................... 378/62 |

FOREIGN PATENT DOCUMENTS

| | | |
|---|---|---|
| JP | 2002-044207 A | 2/2002 |
| JP | 2003-256082 A | 9/2003 |
| JP | 2006-250729 A | 9/2006 |
| JP | 2008-083031 A | 4/2008 |
| JP | 2008-129231 A | 6/2008 |
| JP | 2009-053661 A | 3/2009 |
| JP | 2009-058733 A | 3/2009 |
| JP | 2009-186389 A | 8/2009 |
| JP | 2009-237230 A | 10/2009 |
| JP | 2011-112921 A | 6/2011 |
| JP | 2012-063326 A | 3/2012 |
| JP | 2012-139257 A | 7/2012 |
| JP | 2013-072809 A | 4/2013 |
| WO | 2011-064987 A1 | 6/2011 |

OTHER PUBLICATIONS

Office Action issued by JPO on Sep. 3, 2013 in connection with corresponding Japanese Patent Application No. 2011-213317.
Cannon, Digitial Radiography System CXDI-70C Wireless Premium Portable Flat Panel Detector, 2010, Virtual Imaging, Inc. A Cannon U.S.A. Company.

* cited by examiner

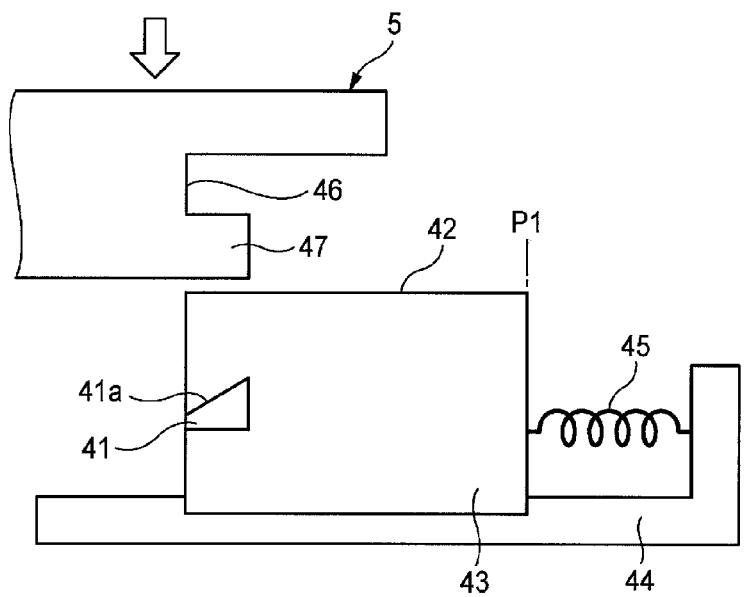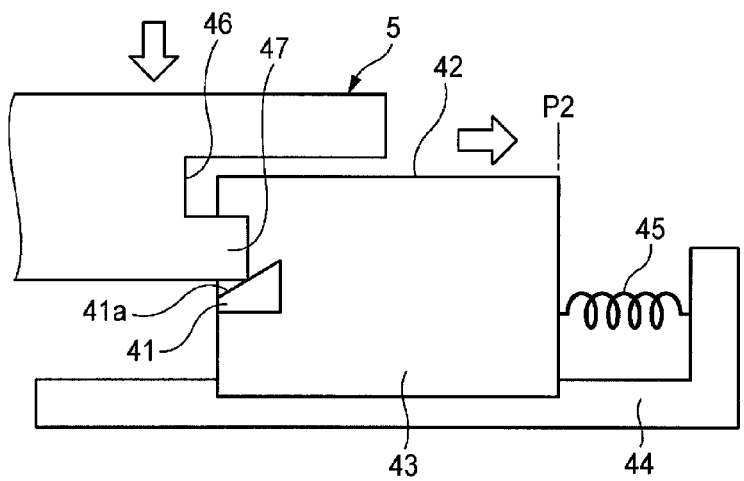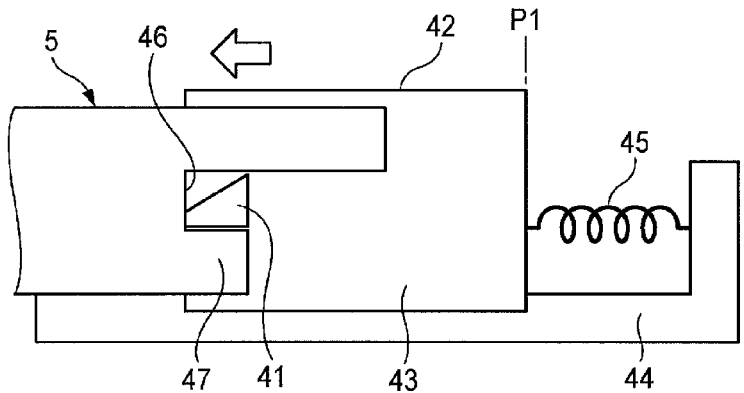

RADIOLOGICAL IMAGE DETECTION APPARATUS

CROSS-REFERENCE TO RELATED APPLICATIONS

This application is based on and claims priority under 35 USC 119 from Japanese Patent Application No. 2011-213317 filed on Sep. 28, 2011; the entire content of which is incorporated herein by reference.

BACKGROUND OF THE INVENTION

1. Technical Field

The present invention relates to a radiological image detection apparatus

2. Related Art

An X-ray imaging has been widely used in the field of medical diagnoses or nondestructive inspection. In a general X-ray imaging, X-rays are irradiated to a subject and attenuated while transmitting at each portion of the subject. Then, X-rays transmitted through the subject are detected to obtain X-ray images based on the intensity distributions of X-rays.

As an X-ray detecting medium, there have been used, for example, a combination of an intensifying screen which generates fluorescence when exposed to X-rays and a film photosensitive to the fluorescence, or a photostimulable phosphor (accumulative phosphor) panel that accumulates the intensity distributions of X-rays as latent images when exposed to X-rays and emits fluorescence in accordance with the latent images by a subsequent irradiation of an excited light such as laser.

Recently, a flat panel detector (FPD) has also been used as an X-ray detecting medium, which generates a digital image data by using a semiconductor device that detects X-rays and converts the detected X-rays into an electric signal, and a so-called electronic cassette configured to accommodate the FPD in a portable case has been put into practical use.

The electronic cassette typically is equipped with a battery that supplies an operation power to the FPD mounted therein. The battery may be attachable to and detachable from the cassette for recharging and exchanging according to degradation caused by repetition of recharging and discharging, respectively (see, for example, Patent Document 1(JP-A-2006-250729)).

In the cassette disclosed in Patent Document 1, a battery is accommodated in a battery accommodating part of a case, and an opening portion of the accommodating part is closed by a cover, such that the battery is fixed to the accommodating part. This cover is locked by a slide type lock attached to the case, such that the opening thereof is controlled.

SUMMARY OF THE INVENTION

The cassette is used while being carried in various places. For example, when the cassette is slid on an installation surface at the time of installing the cassette and a lock mechanism is disposed at a contact surface at which the cassette contacts the installation surface, the lock mechanism may be mistakenly released due to the sliding.

An illustrative aspect of the invention is to provide a radiological image detection apparatus where the fixing of a battery can be ensured.

According to an aspect of the invention, a radiological image detection apparatus includes: a radiological image sensor configured to detect radiation to generate image data; a case configured to accommodate the radiological image sensor therein; a battery accommodated in a battery accommodating part installed in the case and configured to supply an operation power to the radiological image sensor; and a lock mechanism configured to lock and fix the battery accommodated in the battery accommodating part, in which: the lock mechanism includes at least one first lock mechanism and at least one second lock mechanism, each including a coupling member moving between a coupling position at which the lock mechanism is coupled to the battery and a non-coupling position, the coupling member is installed with a manipulation part exposed to an outer surface of a portion of the case in which the battery accommodating part is installed, and the first lock mechanism sets a first direction of a movement direction of the corresponding coupling member from the coupling position to the non-coupling position and the second lock mechanism sets a second direction of a movement direction of the corresponding coupling member from the coupling position to the non-coupling position, being different from the first direction.

In accordance with the radiological image detection apparatus discussed above, plural lock mechanisms of the first and second lock mechanisms are provided. And in the first lock mechanism and second lock mechanisms, the movement directions from a coupling position of a coupling member coupled to a battery to a non-coupling position thereof are different, such that the possibility that the first and second lock mechanisms will be simultaneously released may be reduced. As a result, the fixing of the battery may be ensured.

BRIEF DESCRIPTION OF THE DRAWINGS

FIGS. 6A to 6C are views each illustrating an operation of the lock mechanism of FIG. 5;

DETAILED DESCRIPTION OF EMBODIMENTS OF THE INVENTION

Figure 1:
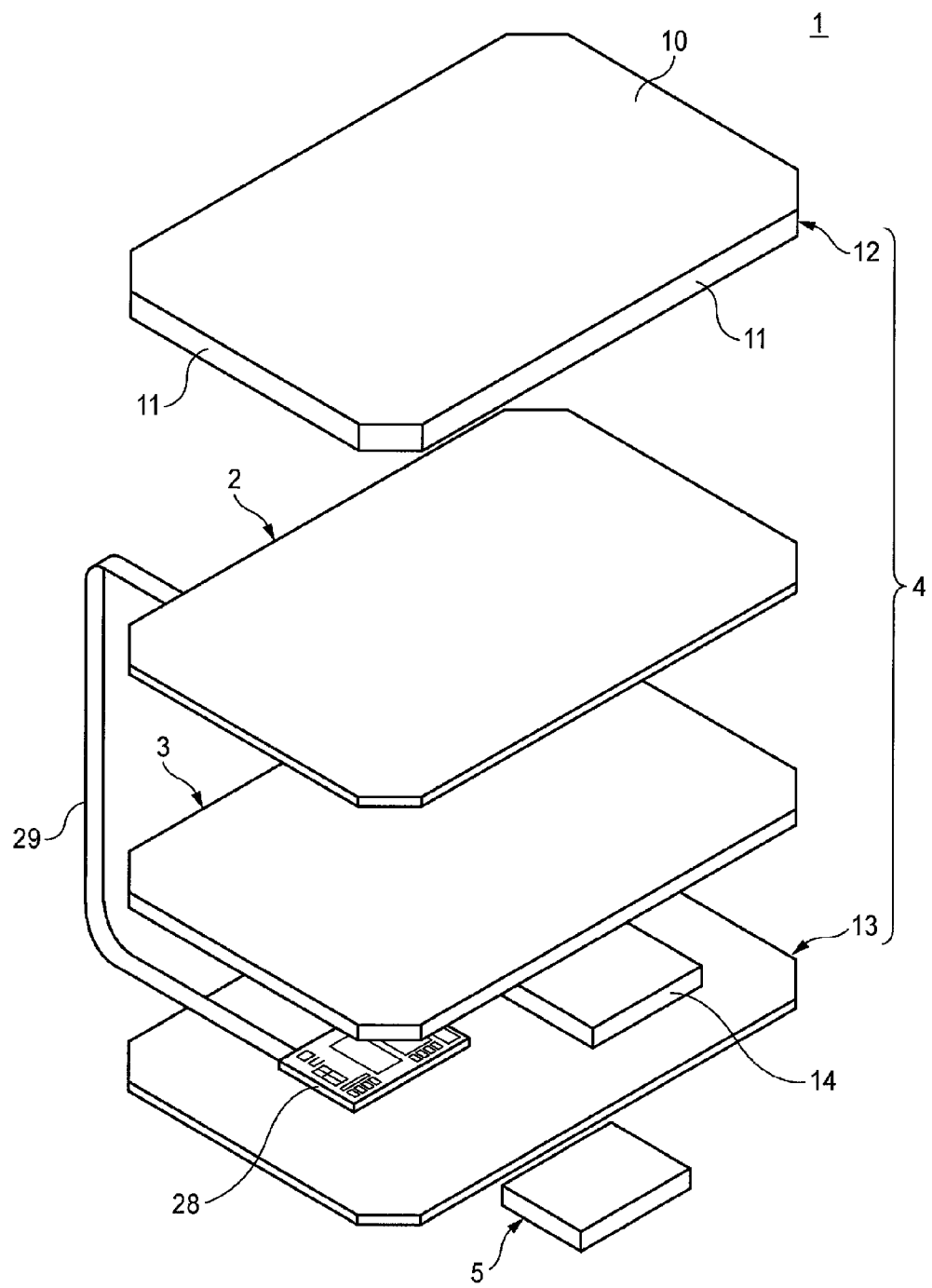
FIG. 1 is an exploded perspective view illustrating a configuration of an example of a radiological image detection apparatus in accordance with an embodiment of the present invention.

FIG. 1 is an exploded perspective view illustrating a configuration of an example of a radiological image detection apparatus in accordance with an embodiment of the present invention.

The X-ray image detection apparatus 1 illustrated in FIG. 1 is so-called an electronic cassette, and is configured to include a flat panel detector (FPD) 2, a base 3 supporting the FPD 2, a case 4 accommodating the FPD 2 and the base 3, and a battery 5 supplying an operation power to the FPD 2.

The case 4 is constituted with a ceiling plate part 10 having an approximately rectangular shape, a front member 12 having frame-type sidewall parts 11 installed to be erected at edges of four sides of the ceiling plate part 10, and a back member 13 blocking a bottom part of the front member 12 from being opened. The front member 12 and the back member 13 are combined to each other to form a closed space having a light-shielded box shape, such that the FPD 2 and the base 3 are accommodated in the closed space.

The X-rays passing through a subject transmit the ceiling plate part 10 of the front member 12 to be incident on the FPD 2 accommodated in the case 4. The ceiling plate part 10 is formed of a material having an excellent X-ray transmissivity, and typically formed of a light metal material such as, for example, aluminum or magnesium, or a resin material such as a carbon fiber reinforced plastics (CFRP), in consideration of a strength-to-weight ratio.

In addition, in the X-ray image detection apparatus 1, the ceiling plate part 10 and the sidewall part 11 of the front member 12 may be integrally formed of the same material, such that the rigidity of the front member 12 is improved, and specifically, the torsional resistance of the ceiling plate part 10 is improved.

When aluminum or magnesium is used as a material to form the ceiling plate part 10 and the side wall part 11 as described above, the ceiling plate part 10 and the side wall part 11 may be integrally formed by, for example, a die-cast molding. Further, when the CFRPs are used, the ceiling plate part 10 and the side wall part 11 may be integrally formed by, for example, a compression molding.

As illustrated in FIG. 1, by integrally forming the ceiling plate part 10 and the side wall part 11, four corners of the front member 12 are chamfered.

The back member 13 constituting a bottom part of the case 4 is installed with a battery accommodating part 14 which accommodates the battery 5. Details of the back member 13 will be described below.

The back member 13 is also formed using typically a light metal material such as aluminum or magnesium, or the resin material such as CFRP in consideration of the strength-to-weight ratio.

Figure 2:
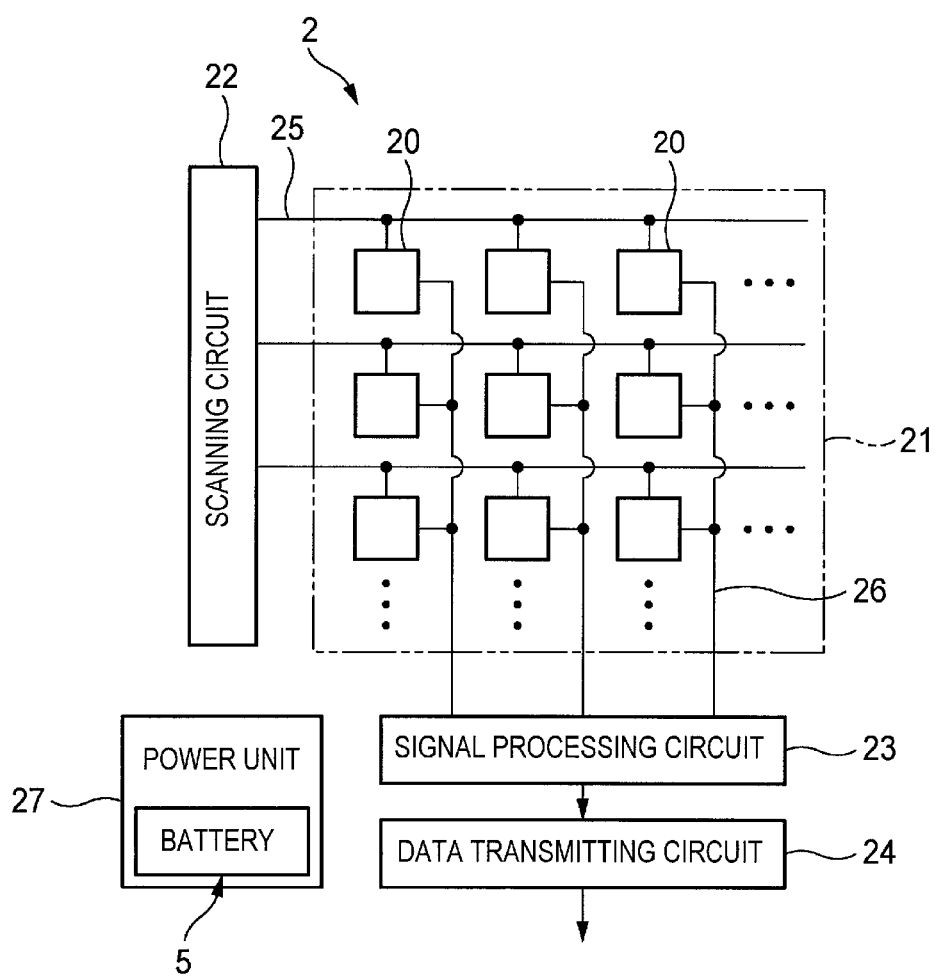
FIG. 2 is a view illustrating a configuration of a radiological image sensor of the radiological image detection apparatus of FIG. 1.

FIG. 2 illustrates a configuration of the FPD 2.

The FPD 2 is constituted with an image receiving unit 21 formed by two-dimensionally arranging a plurality of pixels 20 converting the X-rays into electric charges to accumulate the electric charges on an active matrix thin film transistor (TFT) array substrate, a scanning circuit 22 controlling a reading-out timing of the electric charges from the image receiving unit 21, a signal processing circuit 23 reading the electric charges accumulated in each pixel 20 and converting the read-out electronic charges into image data to store the image data, and a data transmitting circuit 24 transmitting the image data to an external device. The scanning circuit 22 and each pixel 20 are connected to each other for each row by scanning lines 25, and the signal processing circuit 23 and each pixel 20 are connected to each other for each column by signal lines 26.

Each pixel 20 may be configured as a direct conversion type device which directly converts the X-rays into the electric charges at a conversion layer (not illustrated) made of, for example, amorphous selenium, and accumulates the converted electric charges in a capacitor connected to an electrode of a lower portion of the conversion layer. In addition, each pixel 20 may be configured as an indirect conversion type X-ray detecting device which converts X-rays into visible rays first using a scintillator (not illustrated) made of for example, gadolinium oxide ($Gd_2O_3$), sulfated gadolinium ($Gd_2O_2S$) or cesium iodide (CsI), and then converts the converted visible rays into the electronic charges using a photodiode (not illustrated) to accumulate the converted electronic charges.

In each pixel 20, a TFT serving as a switching device (not illustrated) is connected thereto, and a gate electrode of the TFT switch is connected to the scanning line 25, a source electrode thereof is connected to the capacitor, a drain electrode thereof is connected to the signal line 26, respectively. When the TFT switch is turned ON by a driving pulse from the scanning circuit 22, the electric charge accumulated in the capacitor is read-out to the signal line 26.

The signal processing circuit 23 is constituted with an integrating amplifier circuit, an analog to digital (A/D) converter, a correcting circuit, and a video memory (all not illustrated). The integrating amplifier circuit integrates the electric charges output from each pixel 20 through the signal line 26, converts the integrated electric charges into a voltage signal (an image signal), and inputs the voltage signal into the A/D converter. The A/D converter converts the input image signal into digital image data to input the digital image data into the correction circuit. The correction circuit performs a correction such as, for example, an offset correction or a gain correction on the image data to store the corrected image data in the video memory.

Each pixel 20 and each of the circuits 22 to 24 described above are supplied with an operation power from a power unit 27 including the battery 5. Here, wirings connecting the power unit 27, each pixel 20, and each of the circuits 22 to 24 to each other are not illustrated.

Figure 3:
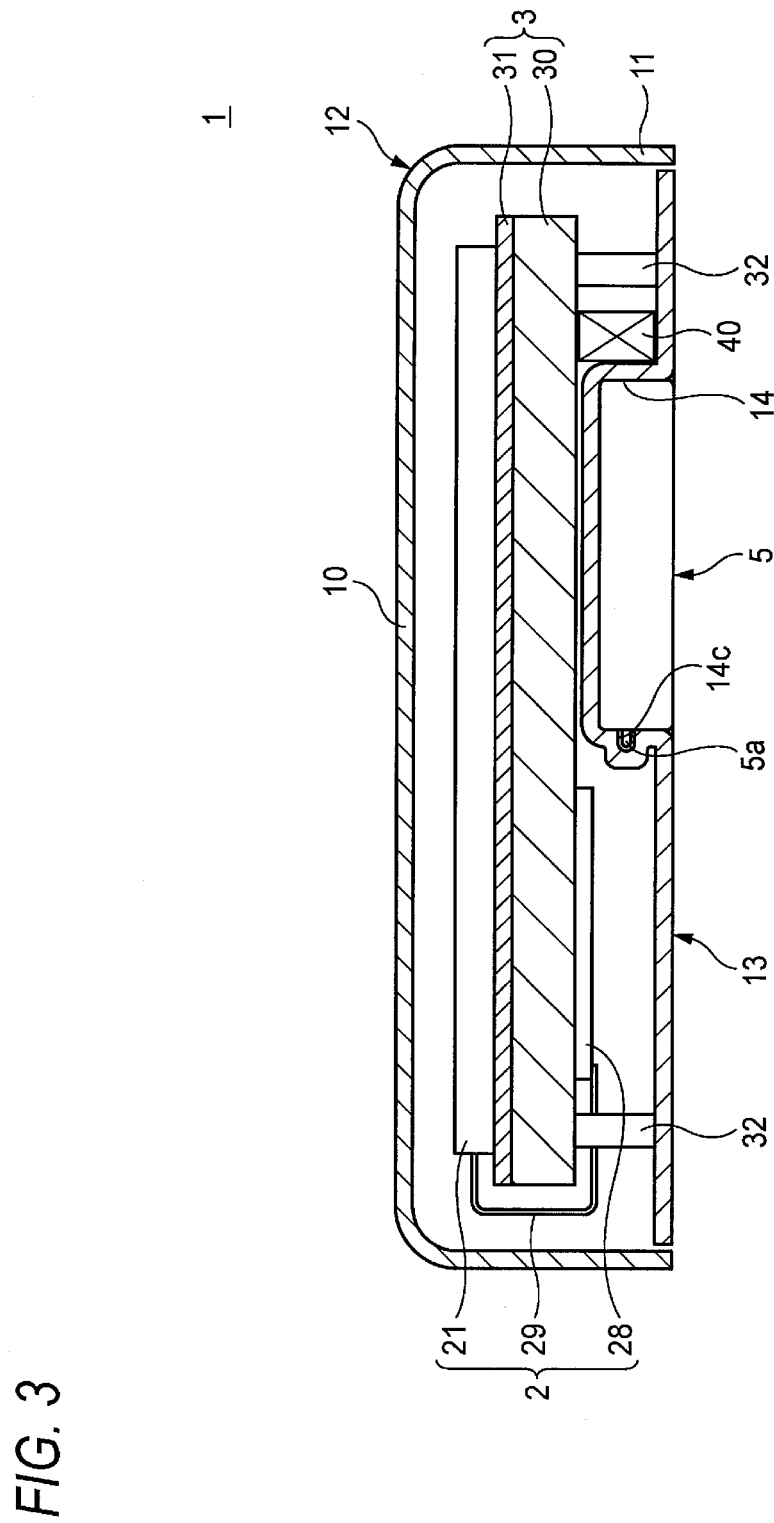
FIG. 3 is a cross-sectional view illustrating an inner configuration of the radiological image detection apparatus of FIG. 1.
Figure 4:
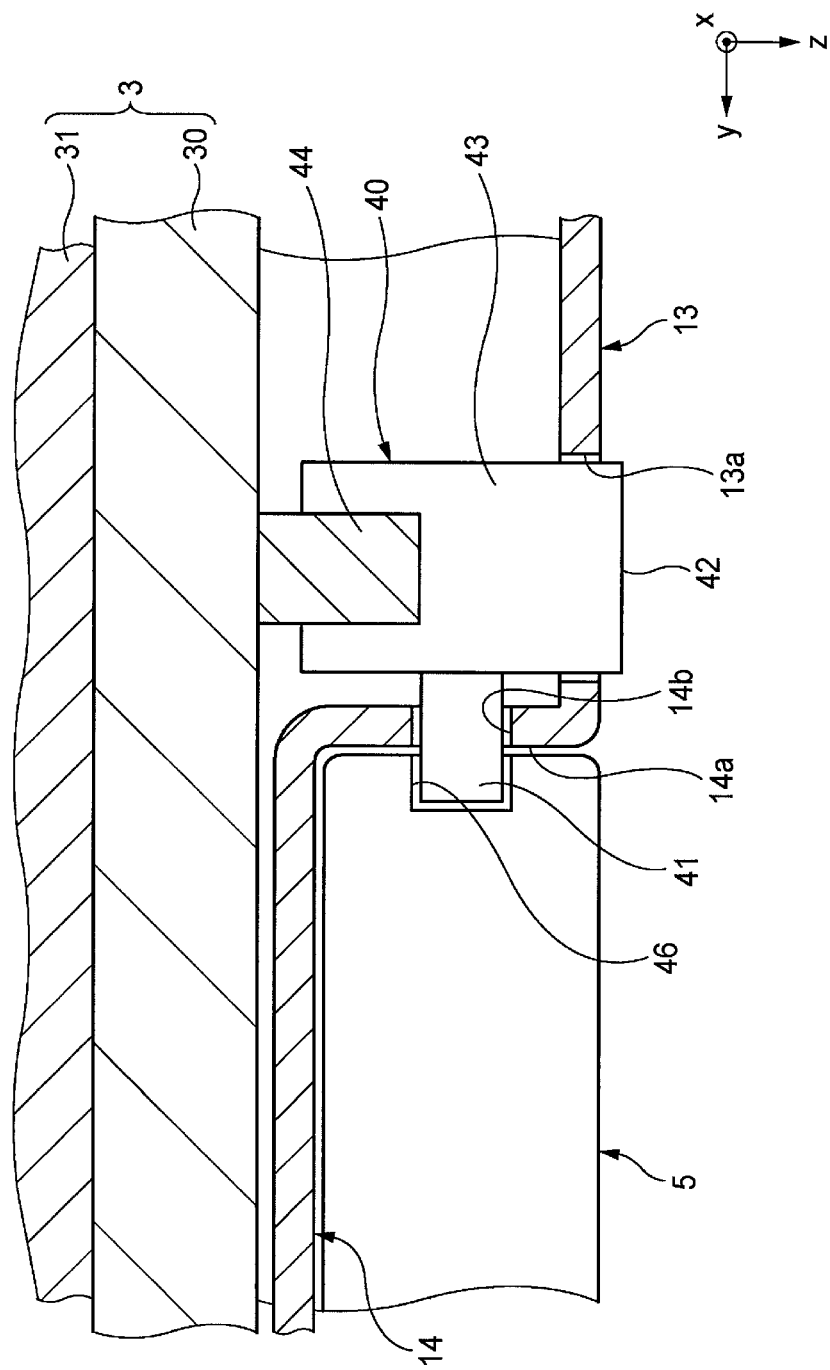
FIG. 4 is an enlarged cross-sectional view illustrating a configuration of a battery accommodating part and its neighboring components of the radiological image detection apparatus of FIG. 1.

FIG. 3 illustrates a cross-sectional view of the configuration of the X-ray image detection apparatus 1, and FIG. 4 illustrates a battery accommodating part 14 and its neighboring components.

In the FPD 2, the image receiving unit 21 is attached to a surface of the base 3 facing the ceiling plate part 10, and a circuit board 28 having the scanning circuit 22 (See FIG. 2), the signal processing circuit 23, or the like, mounted thereon, is attached to other surface of the base 3, respectively, such that the image receiving unit 21 and the circuit board 28 are supported by the base 3. The image receiving unit 21 and the circuit board 28 may be connected to each other using a flexible circuit board 29.

The base 3 is configured to include a base material 30 having a relatively excellent rigidity. In addition, the base 3 is formed by stacking an X-ray shielding material 31 on the base material 30 for shielding the circuit board 28 attached to the other surface of the base 2 from the X-rays in the illustrated example. Further, the base 3 serves to reinforce the TFT array substrate of the FPD2 because of the rigidity.

As the base material 30, for example, a light metal material such as, for example, aluminum or magnesium, or a resin material such as the CFRP, or the like may be used in consideration of the strength-to-weight ratio. In addition, as the X-ray light-shielding material 31, a heavy metal material having an excellent X-ray absorption capability such as, for example, lead, tungsten or molybdenum may be used.

The base 3 is fixed to the back member 13 while having an appropriate spacer 32 interposed between the base 3 and the back member 13 so as not to interfere with the battery accommodating part 14 installed in the back member 13.

In the X-ray image detection apparatus 1 in accordance with the present embodiment, the battery accommodating part 14 is configured as a concave part which is formed by a molding such that a portion of the back member 13 is protruded toward the ceiling plate part 10 of the front member 12. Alternatively, the battery accommodating part 14 may also be configured by a housing member having a similar concave part, separately from the back member 13. In this case, the back member 13 is provided with an appropriate opening part on which the above-mentioned housing member is mounted, and the housing member is mounted on the opening part by an appropriate method such as an adhesion.

One of the sidewall parts surrounding four sides of the battery accommodating part 14 is provided with a coupling concave part 14c to which a hook 5a formed at an edge of the battery 5 facing the one sidewall of the battery accommodating part is coupled. Further, another sidewall part except for a sidewall part in which the coupling concave part 14c is formed (that is, an sidewall part opposite to the sidewall part having the coupling concave part 14c formed therein illustrated in FIG. 3) is installed with a lock mechanism 40 for locking and fixing the battery 5 accommodated in the battery accommodating part 14. The battery 5 is fixed in the battery accommodating part 14 by coupling the hook 5a to the coupling concave part 14c to be locked and fixed by the lock mechanism 40.

The lock mechanism 40 includes a coupling member 43 having a convex part 41 coupled to the battery 5 accommodated in the battery accommodating part 14 and a manipulation part 42 installed therein. In the four sidewall parts surrounding the battery accommodating part 14, the sidewall 14a to which the lock mechanism 40 is installed adjacently is provided with a window 14b, and the convex part 41 of the coupling member 43 passes through the window 14b to be protruded to an inner portion of the battery accommodating part 14. In addition, the manipulation part 42 of the coupling member 43 passes through a window 13a formed at the back member 13 to be exposed to an outer surface of the back member 13.

In the X-ray image detection apparatus 1, the base 3 is made of a higher rigidity material than that of the back member 13 in which the battery accommodating part 14 is installed, and the lock mechanism 40 is fixed to and supported by the base 3. The base material 30 constituting the base 3 and the back member 13 is typically made of a light metal material such as, for example, aluminum or magnesium, or a resin material such as the CFRP. For example, when the base 3 and the back member 13 are made of the same material, the base 3 may be formed to have a high rigidity by forming the base 3 to be thicker than the back member 13. Generally, the X-ray image detection apparatus has an external size determined by the standard, and under this limitation, in order to secure an inner space of the case accommodating the FPD 2 as much as possible, the front member 12 or the back member 13 is formed to be relatively thin. The base 3 accommodated in the case securing the space as described above may easily have a thickness thicker than that of the front member 12 or the back member 13.

In addition, a dimension of the lock mechanism 40 in a direction vertical to the outer surface of the back member 13 may be equal to or smaller than a depth of the concave part configuring the battery accommodating part 14. This is because when the dimension of the lock mechanism 40 is larger than the depth of the concave part, an unnecessary gap is formed between a concave surface of the concave part and the base 3. The dimension of the lock mechanism 40 is formed to be equal to or smaller than the depth of the concave part, and, as a result, the entire thickness of the X-ray image detection apparatus 1 can be formed to be thin as much as possible without forming the unnecessary gap as illustrated in FIG. 3. In other words, a central portion of the X-ray image detection apparatus may be maximally secured within the external size determined by the standard. Therefore, the thickness of the base 3 may be secured to be large as described above, and the resistance against an impact of the X-ray image detection apparatus when dropped may be improved.

Figure 5:
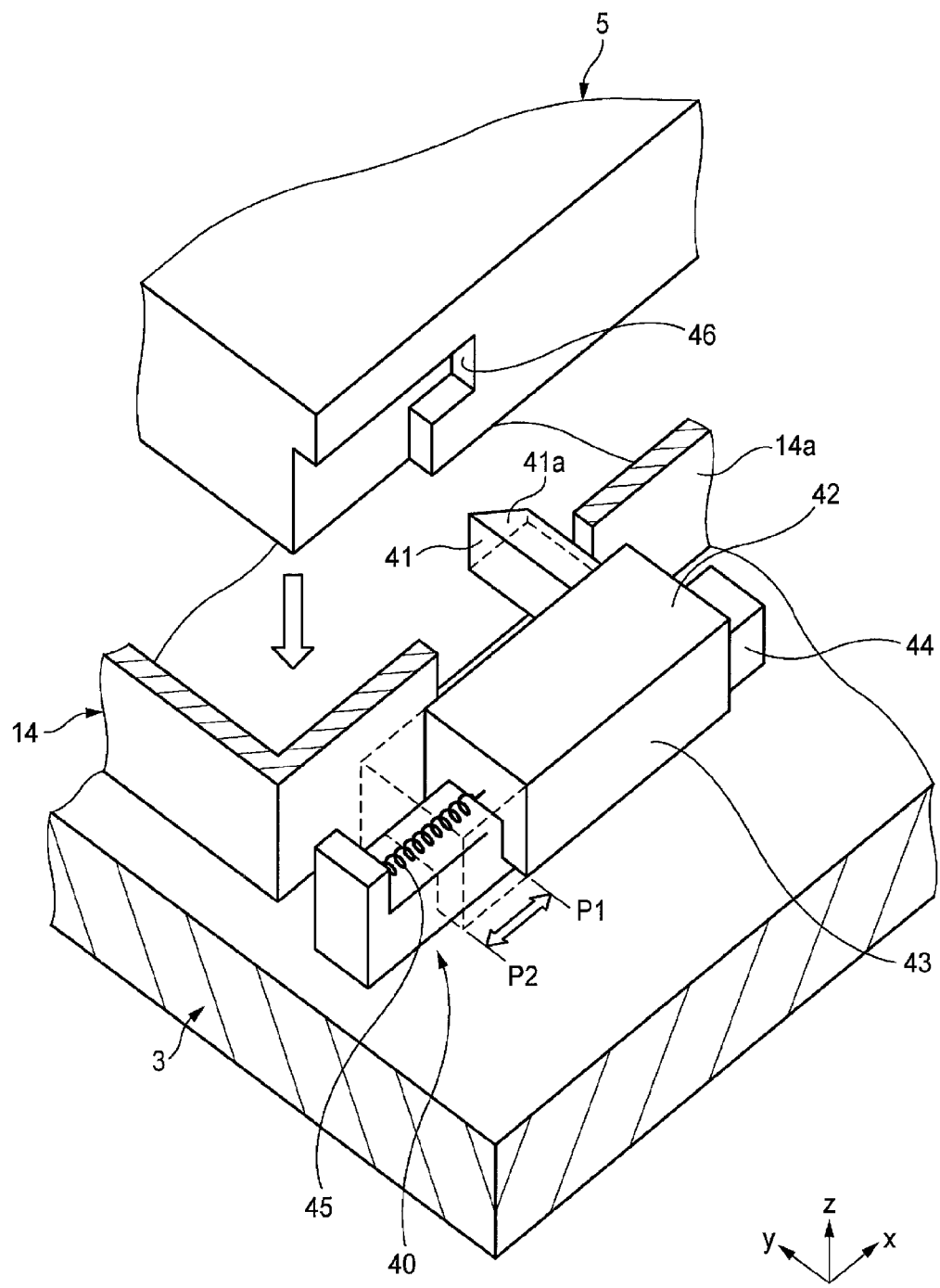
FIG. 5 is a perspective view illustrating a configuration of an example of a lock mechanism used in the radiological image detection apparatus of FIG. 1.

FIG. 5 illustrates a configuration of the lock mechanism 40.

The lock mechanism 40 includes the coupling member 43 as described above, a guide rail, and a spring 45. The coupling member 43 is formed of a slider moving along the guide rail 44 which movably supports the slider 43. The spring 45 presses the slider 43 moving along the guide rail 44 in a movement direction of the slider 43. In this configuration, the guide rail 44 is fixed to the base 3, and the lock mechanism 40 is supported by the base 3.

A concave part 46 coupled to the convex part 41 of the slider 43 is formed in a side part of the battery 5 facing the sidewall part 14a of the battery accommodating part 14 to which the lock mechanism is installed adjacently. When the slider 43 is positioned at an end part (a coupling position) of one side of the guide rail 44, the convex part 41 of the slider 43 and the concave part 46 of the battery 5 are coupled to each other. When the slider is positioned at an end part (a non-coupling position) of the other side of the guide rail 44, the coupling between the convex part 41 of the slider 43 and the concave part 46 of the battery 5 is released. The spring 45 presses the slider 43 so that the slider 43 moves from the non-coupling position to the coupling position. In the lock mechanism 40, the convex part 41 of the slider 43 is coupled to the concave part 46 of the battery 5 to lock the battery 5, thereby maintaining the battery 5 in the battery accommodating part 14.

In the lock mechanism 40, the guide rail 44 is formed to be in approximately parallel with the outer surface of the back member 13 in which the battery accommodating part 14 is installed, and to be extended and installed in a direction (an X axis direction in FIG. 5) along the sidewall part 14a of the battery accommodating part 14 to which the lock mechanism 40 is installed adjacently. Therefore, an operational direction (a lock-release direction) of the manipulation part 42 moving the slider 43 from the coupling position to the non-coupling position is a straight line direction along the sidewall part 14a of the battery accommodating part 14 to which the lock mechanism 40 is installed adjacently.

FIGS. 6A to 6C illustrate an operation of the lock mechanism 40.

When the battery 5 is mounted on the battery accommodating part 14, first of all, the spring 45 presses the slider 43 to be positioned at the coupling position P1 (FIG. 6A). When the battery 5 is inserted into the battery accommodating part 14, the convex part 41 of the slider 43 comes into contact with a shoulder part 47 which is in continuous with the concave part 46 of the battery 5. Since a contact surface 41a of the convex part 41 contacting the shoulder part 47 is formed in an inclined surface having a gradient in the X axis direction, as the battery 5 is inserted into the battery accommodating part 14, the shoulder part 47 pushes the slider 43 into the non-coupling position P2 against the pressing force of the spring 45 while sliding on the inclined surface 41a of the convex part 41 (FIG. 6B). When the battery 5 is completely inserted into the battery accommodating part 14, the convex part 41 slides over the shoulder part 47 to arrive at a position toward the concave part 46 in the movement direction of the slider 43, and at that position, the slider 43 is pressed by the spring 45 to be returned automatically to the coupling position P1 and the convex part 41 is entered into and coupled to the concave part 46 (FIG. 6C). Even though the slider 43 is excessively pushed, the force is distributed due to the presence of the inclined surface 41a, and the damage can be prevented.

When the battery 5 is detached from the battery accommodating part 14, the manipulation part 42 of the slider 43 exposed to the outer surface of the back member 13 is manipulated by a user in the lock-release direction to move the slider 43 from the coupling position to the non-coupling position. As a result, the coupling between the convex part of the slider and the concave part of the battery is released making the battery to be in a detachable state. When the battery is detached from the battery accommodating part and the manipulating of the manipulation part is released, the slider is pressed by the spring to be returned automatically to the coupling position.

Figure 7:
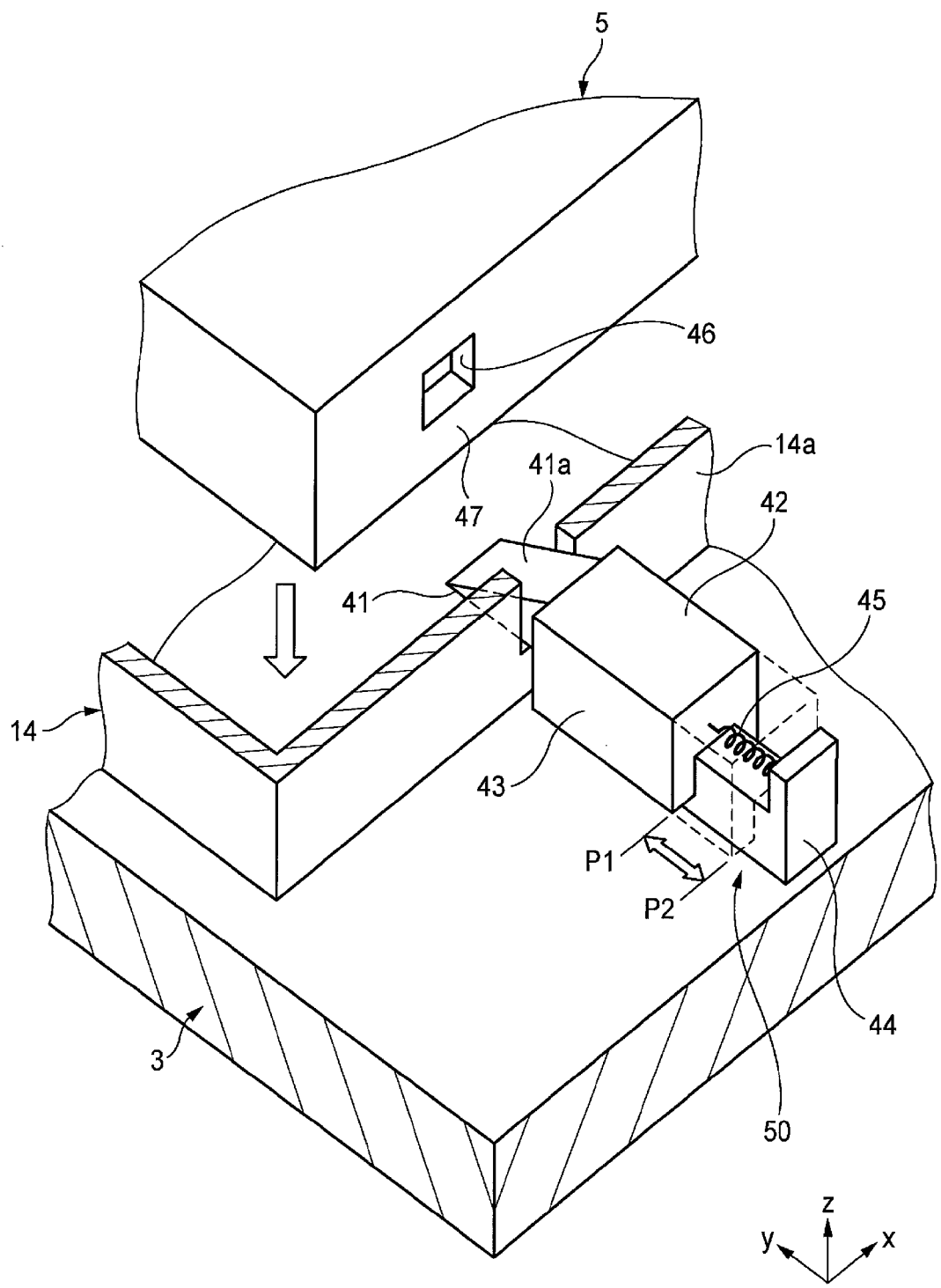
FIG. 7 is a perspective view illustrating a configuration of another example of the lock mechanism.

FIG. 7 illustrates a configuration of another example of the lock mechanism.

A lock mechanism 50 illustrated in FIG. 7 is different from the lock mechanism 40 illustrated in FIG. 5 in that a guide rail 44 is extended to be installed in a direction (a Y axis direction in FIG. 7) approximately perpendicular to a sidewall part 14a of a battery accommodating part 14 to which the lock mechanism 50 is installed adjacently. Further, an operational direction (a lock-release direction) of a manipulation part 42 moving a slider 43 from a coupling position P1 to a non-coupling position P2 is in a straight line direction approximately perpendicular to the sidewall part 14a of the battery accommodating part 14 to which the lock mechanism 50 is installed adjacently. Other components are the same as those of the lock mechanism 40 illustrated in FIG. 5.

When the battery 5 is mounted on the battery accommodating part 14, first of all, the spring 45 presses the slider 43 to be positioned at the coupling position P1. When the battery 5 is inserted into the battery accommodating part 14, the convex part 41 of the slider 43 comes into contact with a shoulder part 47 which is in continuous with the concave part 46 of the battery 5. Since a contact surface 41a of the convex part 41 contacting the shoulder part 47 is formed in an inclined surface having a gradient in the Y axis direction, the battery 5 is inserted into the battery accommodating part 14, the shoulder part 47 pushes the slider 43 into the non-coupling position P2 against pressing force of the spring 45 while sliding on the inclined surface 41a of the convex part 41. When the battery 5 is completely inserted into the battery accommodating part 14, the convex part 41 slides over the shoulder part 47 to arrive at a position toward the concave part 46 in the movement direction of the slider 43. And at that position, the slider 43 is pressed by the spring 45 to be returned automatically to the coupling position P1 and the convex part 41 is entered into and coupled to the concave part 46.

Figure 8:
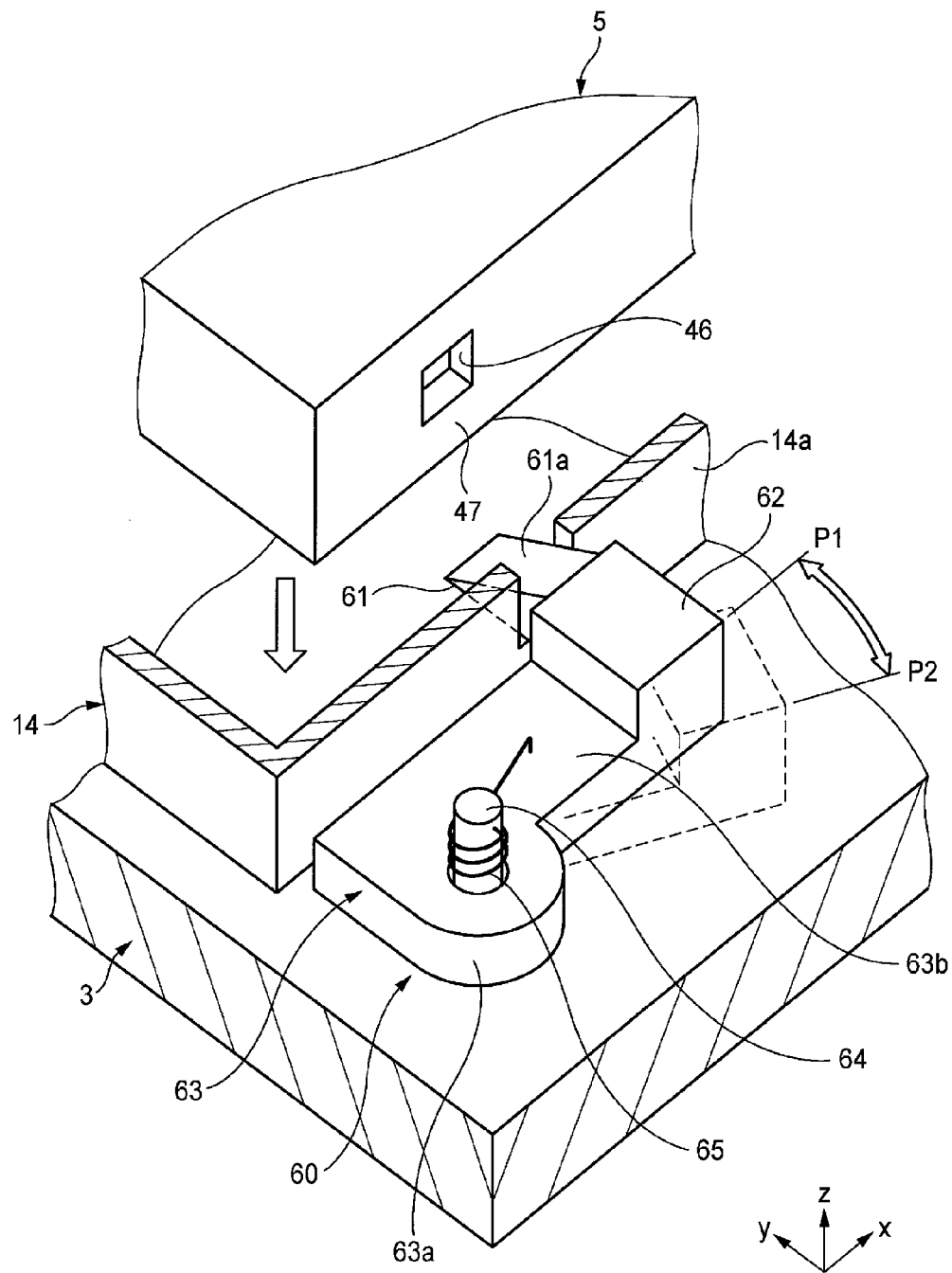
FIG. 8 is a perspective view illustrating a configuration of another example of the lock mechanism.

FIG. 8 illustrates a configuration of another example of the lock mechanism.

A lock mechanism 60 illustrated in FIG. 8 is configured to include a coupling member 63, a shaft member 64, and a spring 65. The coupling member 63, which is a rotating member rotating around a shaft of the shaft member 64, includes a supported part 63a supported by the shaft member 64 and an arm part 63b extended from the supported part 63b. And a convex part 61 and a manipulation part 62 are installed at a front end portion of the arm part 63b. The spring 65 presses the coupling member 63 rotating around the shaft member 64 from a non-coupling position P2 toward a coupling position P1 in a rotation direction thereof. In this configuration, the shaft member 64 is fixed to the base 3, and the lock mechanism 60 is supported by the base 3.

In the example as illustrated in FIG. 8, the shaft member 64 is extended and installed in a direction (a Z axis direction in FIG. 8) approximately perpendicular to an outer surface of the back member 13 at which the battery accommodating part 14 is installed. Therefore, an operational direction (a lock-release direction) of the manipulation part 62 moving the coupling member 63 from the coupling position P1 to the non-coupling position P2 is formed in an arc direction with the shaft member 64 at the center in a plane (an XY plane) approximately parallel with the outer surface of the back member 13.

When the battery 5 is mounted on the battery accommodating part 14, first of all, the spring 65 presses the coupling member 63 to be positioned at the coupling position P1. When the battery 5 is inserted into the battery accommodating part 14, the convex part 61 of the coupling member 63 comes into contact with the shoulder part 47 which is in continuous with the concave part 46 of the battery 5. A contact surface 61a of the convex part 61 contacting the shoulder part 47 is formed with an inclined surface having a gradient in the Y axis direction. And as the battery 5 is inserted into the battery accommodating part 14, the shoulder part 47 pushes the coupling member 63 into the non-coupling position P2 against the pressing force of the spring 65 while sliding on the inclined surface 61a of the convex part 61. When the battery 5 is completely inserted into the battery accommodating part 14, the convex part 61 relatively slides over the shoulder part 47 to arrive a position toward the concave part 46 in the rotation direction of the coupling part 63. And at that position, the coupling member 63 is pressed by the spring 65 to be returned automatically to the coupling position P1 and the convex part 61 is entered into and coupled to the concave part 46.

Figure 9:
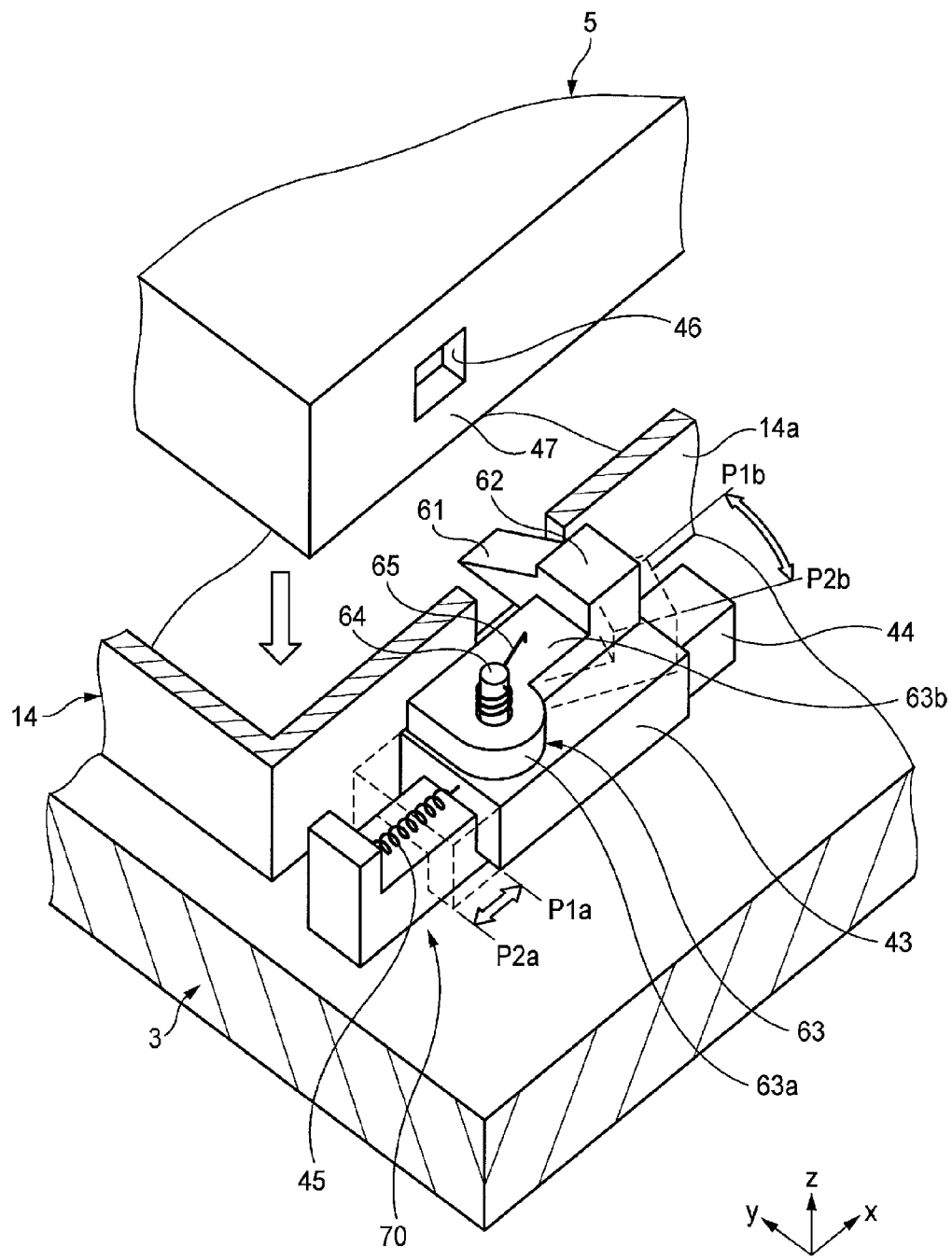
FIG. 9 is a perspective view illustrating a configuration of another example of the lock mechanism.

Meanwhile, the lock mechanism is not limited to the above-mentioned examples. For example, the lock mechanism may have a configuration in which the lock mechanism (the slider 43, the guide rail 44, and the spring 45) illustrated in FIG. 5 and the lock mechanism (the coupling member 63, the shaft member 64, and the spring 65) illustrated in FIG. 8 are combined, as illustrated in FIG. 9. The lock mechanism 70 illustrated in FIG. 9 is configured to include a coupling member 63, a shaft member 64 extended in an Z axis direction, a slider 43, a guide rail 44 extended in an X axis direction, a first spring 45, and a second spring 65. The slider 43 moves along the guide rail 44 which movably supports the slider 43. The shaft member 64 is fixed to the slider 43 and moves along the guide rail 44 integrally with the slider 43. The coupling member 63, which is a rotating member rotating around a shaft of the shaft member 64, includes a supported part 63a supported by the shaft member 64 and an arm part 63b extended from the supported part 63a, and a convex part 61 and a manipulation part 62 are installed at a front end portion of the arm part 63b. The first spring 45 presses the slider 43 which moves along the guide rail 44 in a movement direction thereof from a non-coupling position P2a to a coupling position P1a, and the second spring 65 presses the coupling member 63 which rotates along the shaft member 64 in a rotation direction thereof from a non-coupling position P2b to a coupling position P1b. In this configuration, the guide rail 44 is fixed to the base 3, and the lock mechanism 70 is supported by the base 3.

In the example as illustrated in FIG. 9, an operational direction (a lock-release direction) of the manipulation part 62 moving the coupling member 63 from the coupling position P1b to the non-coupling position P2b is an approximately straight line direction inclined with respect to a sidewall part 14a of a battery accommodating part 14 to which the lock mechanism 70 is installed adjacently by combination with an operational direction of a manipulation part 62 moving the slider 43 from the coupling position P1a to the non-coupling position P2a In accordance with the lock mechanisms 40, 50, 60, and 70 illustrated in FIGS. 5, 7, 8, and 9, when the battery 5 is mounted on the battery accommodating part 14, even when the back member 13 is bent by an external force locally applied to the back member 13 having the accommodating part 14 installed thereon, these lock mechanisms are stably supported by the base 3 having a higher rigidity than that of the back member 13, so that the lock mechanisms can be smoothly operated. Therefore, the locking operation of the battery 5 by the locking mechanism may be ensured. In particular, these lock mechanisms are configured so that the coupling members 43 and 63 are pressed by the springs 45 and 65 and then automatically returned to the coupling position to lock the battery 5. The lock mechanism needs to be stably supported to smoothly perform these operations.

Further, the lock mechanisms 40, 50, 60, and 70 as described above are configured so that the coupling members 43 and 63 are pressed by the springs 45 and 65 and thus automatically returned to the coupling position to lock the battery 5. Therefore, the mounting of the battery is completed by a single action of pushing the battery 5 into the battery accommodating part 14 making it easy to handle the X-ray image detection apparatus.

The guide rail 44 and the shaft member 64 are fixed to the base 3 to be directly supported by the base 3 in all of the lock mechanisms 40, 50, 60, and 70 as described above. However, the guide rail 44 and the shaft member 64 are fixed to the back member 13 to be indirectly supported by the base 3 through the back member 13 in a lock mechanism to be described below.

Figure 10:
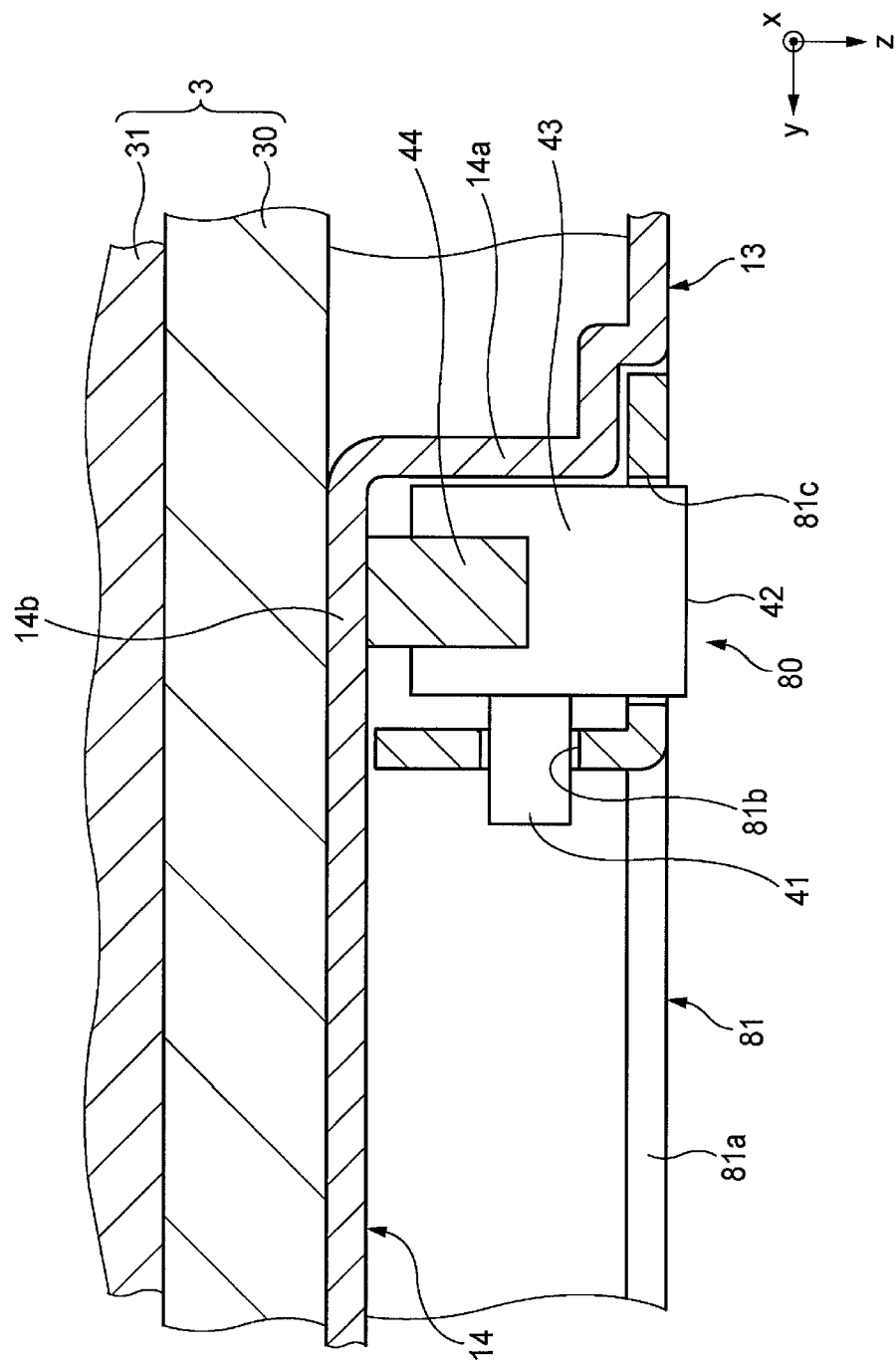
FIG. 10 is a cross-sectional view illustrating a configuration of another example of the lock mechanism.

FIG. 10 illustrates a configuration of a modified example of the lock mechanism illustrated in FIG. 5.

A lock mechanism 80 illustrated in FIG. 10 is installed adjacently to the sidewall part 14a of the battery accommodating part 14 in the battery accommodating part 14, and a guide rail 44 configuring the lock mechanism 80 is fixed to a lower wall part 14b of the battery accommodating part 14. In addition, the lower wall part 14b of the battery accommodating part 14 to which the guide rail 44 is fixed is supported by the base 3 at a surface opposite to the surface having the guide rail 44 fixed thereto. In this configuration, the lock mechanism 80 is indirectly supported by the base 3 through the back member 13.

Further, an exterior member 81 including an opening 81a through which the battery 5 is inserted and removed, and windows 81b and 81c exposing the convex part 41 and the manipulation part 42 of the slider 43, respectively, is adhered to an opening part of the battery accommodating part 14, and the lock mechanism 80 is covered by the exterior member 81.

Since the operations of the lock mechanism 80 are the same as those of the lock mechanism 40 illustrated in FIG. 5, a description thereof will be omitted.

In the lock mechanism 80 in accordance with the present embodiment, when the battery 5 is mounted on the battery accommodating part 14 and even when the back member 13 is bent, the lock mechanism 80 is supported by the base 3 as well as the back member 13, such that the lock mechanism 80 is more stably supported as compared to the case where the back mechanism 80 is supported only by the back member 13 and, therefore, can be smoothly operated. Therefore, the locking operation of the battery 5 by the locking mechanism 80 may be ensured. Further, in the configuration where the lock mechanism 80 is indirectly supported by the base 3 through the back member 13, the base 3 does not necessarily have a higher rigidity than that of the back member 13, but it is preferable that the base 3 has a high rigidity in view of stably supporting the lock mechanism 80. Furthermore, when the rigidity of the back member 13 to which the lock mechanism 80 is fixed is sufficiently secured, the support provided by the base 3 may be omitted.

In the lock mechanism 50 illustrated in FIG. 7 and the lock mechanism 70 illustrated in FIG. 9, the guide rail 44 is fixed to the lower wall part 14b of the battery accommodating part 14, and this lower wall part 14b is supported by the base 3, such that the lock mechanism 50 or 70 may be indirectly supported by the base 3 through the back member 13. Further, in the lock mechanism 60 illustrated in FIG. 8, the shaft member 64 is fixed to the lower wall part 14b of the battery accommodating part 14, and this lower wall part 14b is supported by the base 3, such that the lock mechanism 60 may be indirectly supported by the base 3 through the back member 13.

The X-ray image detection apparatus 1 is configured to have at least two different directions as the lock-release direction of the lock mechanisms using a plurality of lock mechanisms as illustrated in FIG. 5.

Figure 11:
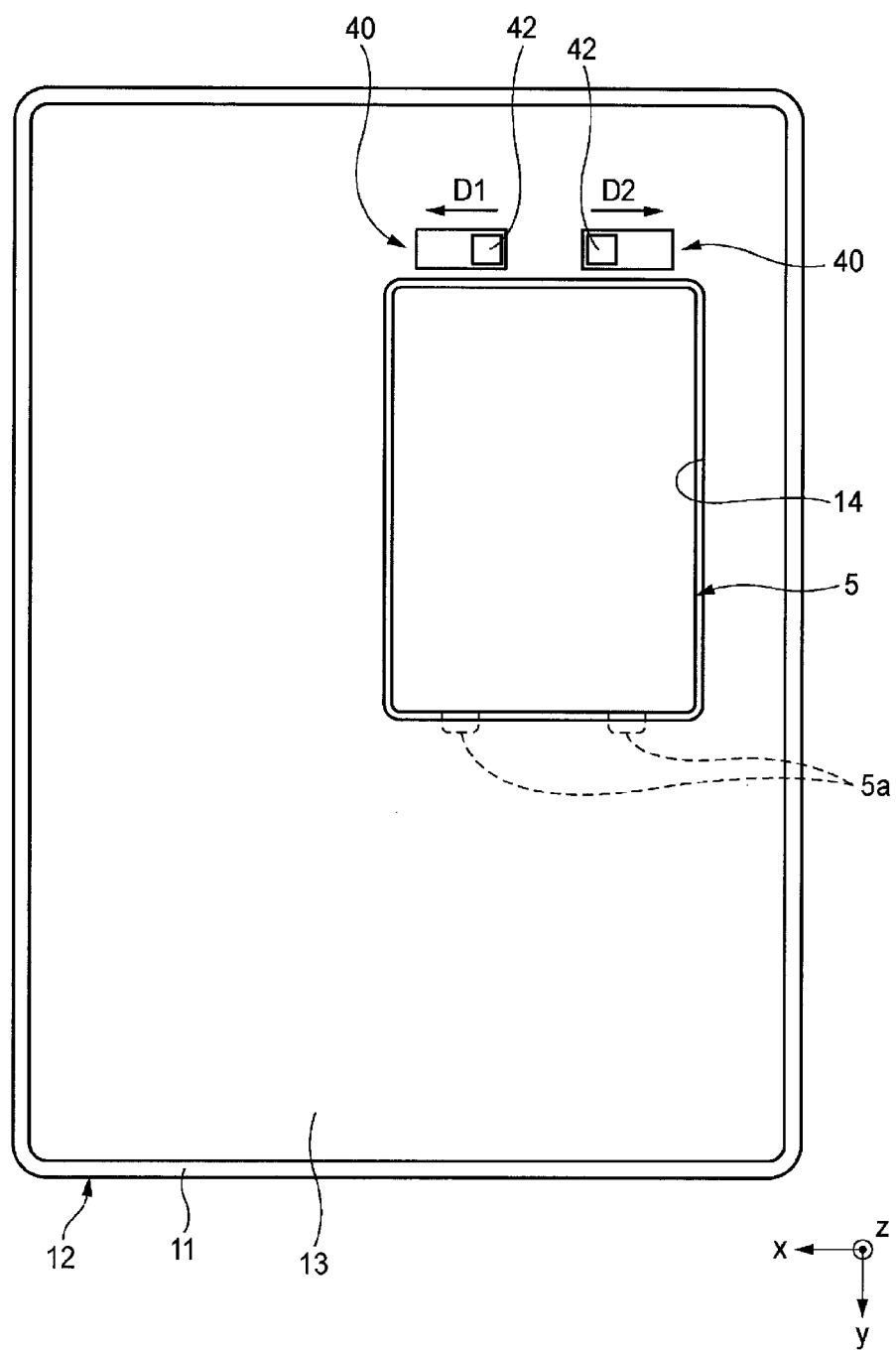
FIG. 11 is a view illustrating an example of placement of lock mechanisms and setting of lock-release directions of the lock mechanisms in the radiological image detection apparatus of FIG. 1.

FIG. 11 illustrates an example of placement of lock mechanisms and setting of a lock-release direction In the example illustrated in FIG. 11, two lock mechanisms 40 as illustrated in FIG. 5 are used, and these lock mechanisms 40 are installed adjacently to a sidewall part opposite to the sidewall part of the battery accommodating part 14 to which the hook 5a of the battery 5 is coupled. Further, a lock-release direction of one lock mechanism 40 is set to a first direction D1 along the sidewall part, and a lock-release direction of the other lock mechanism 40 is set to a second direction D2 opposite to the first direction.

Figure 12:
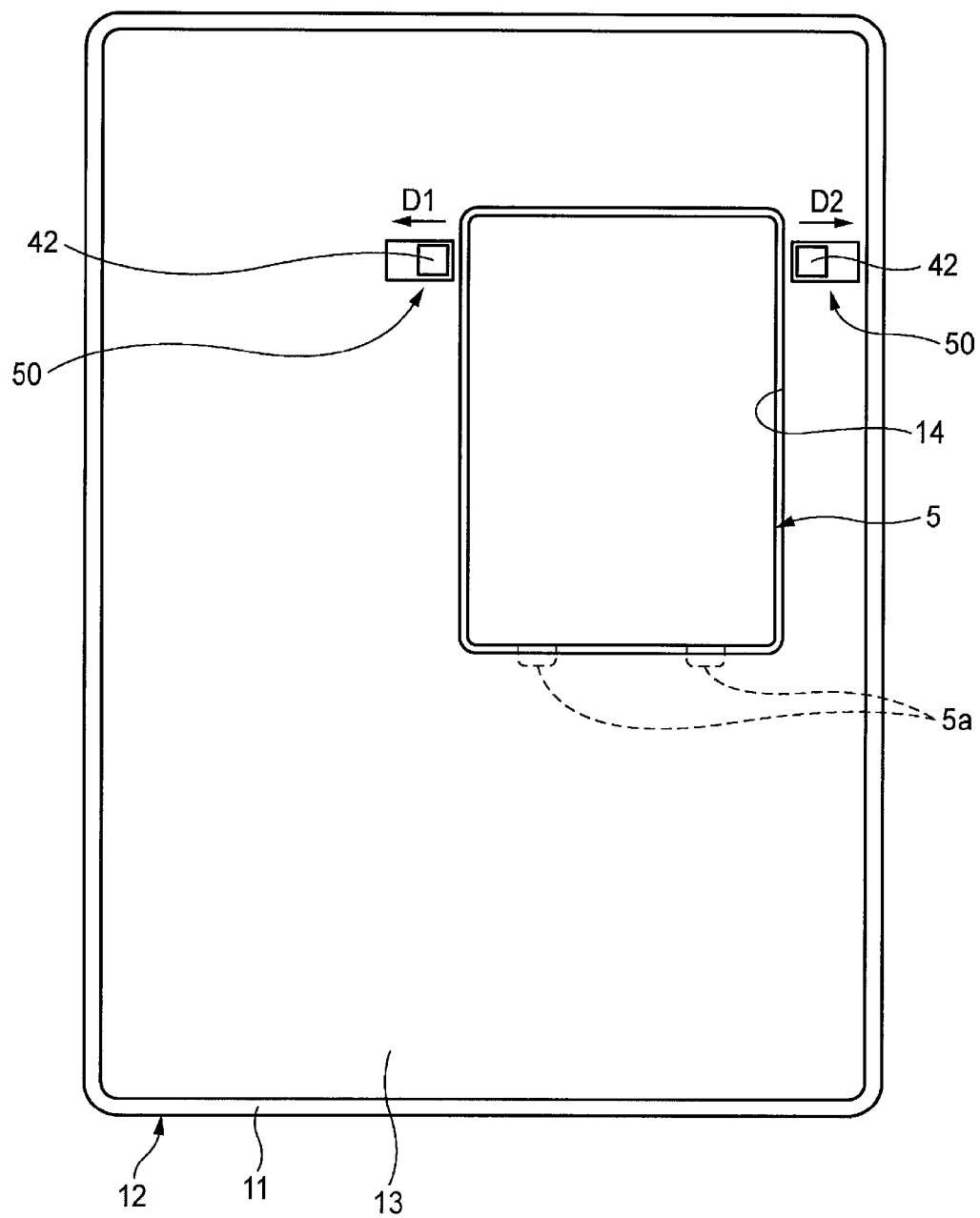
FIG. 12 is a view illustrating another example of placement of lock mechanisms and setting lock-release directions of the lock mechanisms in the radiological image detection apparatus of FIG. 1.

FIG. 12 illustrates another example of placement of lock mechanisms and setting of a lock-release direction.

In the example illustrated in FIG. 12, two lock mechanisms 50 as illustrated in FIG. 7 are used, and these lock mechanisms 50 are each installed adjacently to each of a pair of sidewalls in parallel with each other and intersecting with the sidewall of the battery accommodating part 14 to which the hook 5a of the battery 5 is coupled, respectively. Further, a lock-release direction of one lock mechanism 50 is set to a first direction D1 perpendicular to the sidewall part, and a lock-release direction of the other lock mechanism 50 is set to a second direction D2 opposite to the first direction.

Meanwhile, as illustrated in FIG. 11 or FIG. 12, the lock mechanisms may be installed at an edge opposite to the edge of the battery 5 to which the hook 5a is installed. That is, the lock mechanisms may be disposed as far as possible from a coupling portion of the hook 5a of the battery 5 and the sidewall of the battery accommodating part 14. By disposing the lock mechanism far from the coupling portion, the force stopping the battery 5 may be small, and when the cassette is carried or moved, it becomes more difficult to dislocate.

Figure 13:
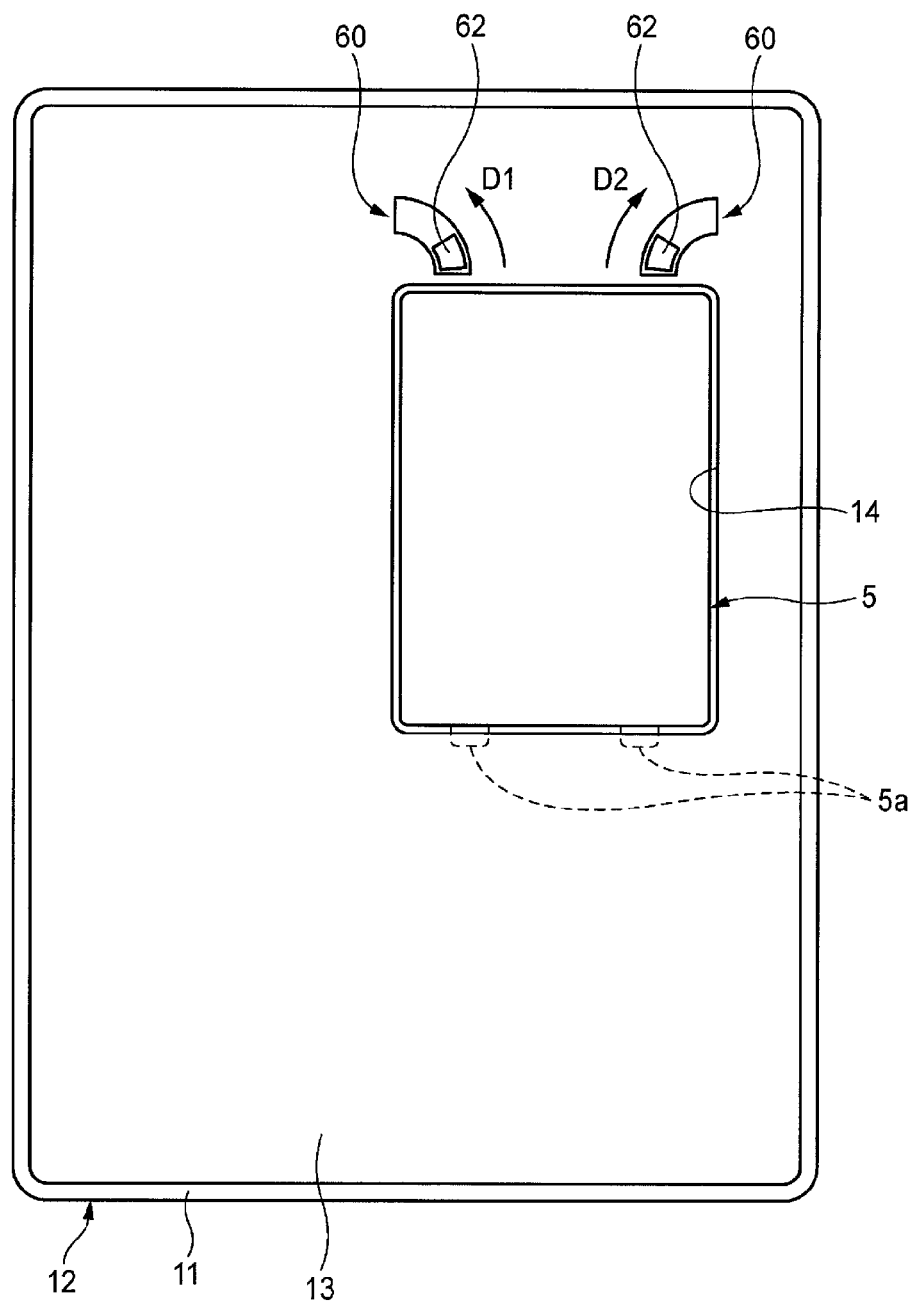
FIG. 13 is a view illustrating an example of placement of lock mechanisms and setting of lock-release directions of the lock mechanisms in the radiological image detection apparatus of FIG. 1.

FIG. 13 illustrates another example of placement of lock mechanisms and setting of a lock-release direction.

In the example illustrated in FIG. 13, two lock mechanisms 60 as illustrated in FIG. 8 are used, and these lock mechanisms 60 are installed adjacently to a sidewall part opposite to the sidewall part of the battery accommodating part 14 to which the hook 5a of the battery 5 is coupled. Further, a lock-release direction of one lock mechanism 60 is set to a first direction D1 which is a clockwise direction in the plane (an XY plane) that is in parallel with the outer surface of the back member 13, and a lock-release direction of the other lock mechanism 60 is set to a second direction D2 which is a counter-clockwise direction opposite to the first direction.

Figure 14:
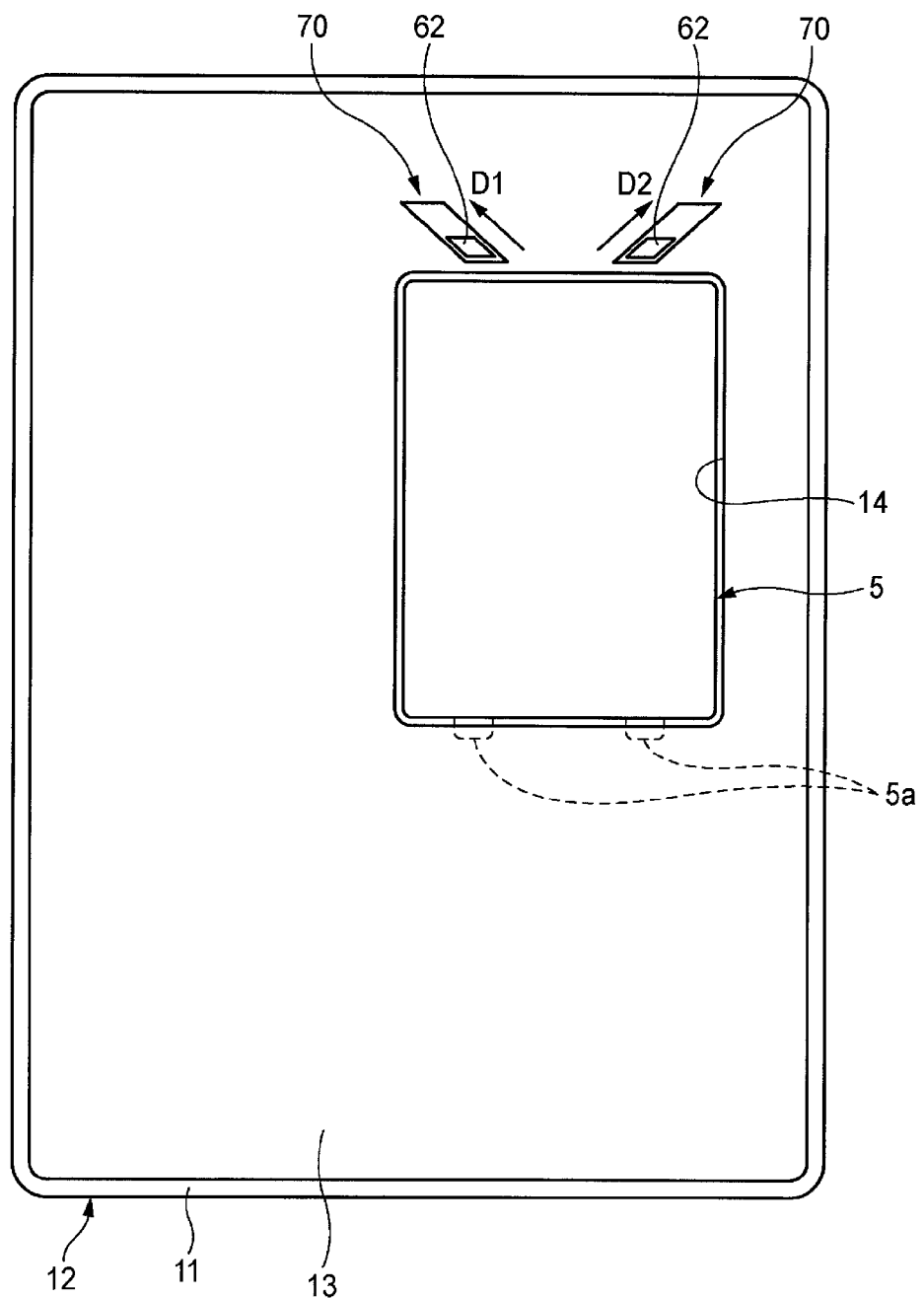
FIG. 14 is a view illustrating another example of placement of lock mechanisms and setting of lock-release directions of the lock mechanisms in the radiological image detection apparatus of FIG. 1.

FIG. 14 illustrates another example of placement of lock mechanisms and setting of a lock-release direction.

In the example illustrated in FIG. 14, two lock mechanisms 70 as illustrated in FIG. 9 are used, and these lock mechanisms 70 are installed adjacently to a sidewall part opposite to the sidewall part of the battery accommodating part 14 to which the hook 5a of the battery 5 is coupled. Further, a lock-release direction of one lock mechanism 70 is set to a first direction D1 inclined at a predetermined angle with respect to the sidewall part, and a lock-release direction of the other lock mechanism 70 is set to a second direction D2 inclined with respect to the side wall part at an angle different from that of the first direction.

Figure 15:
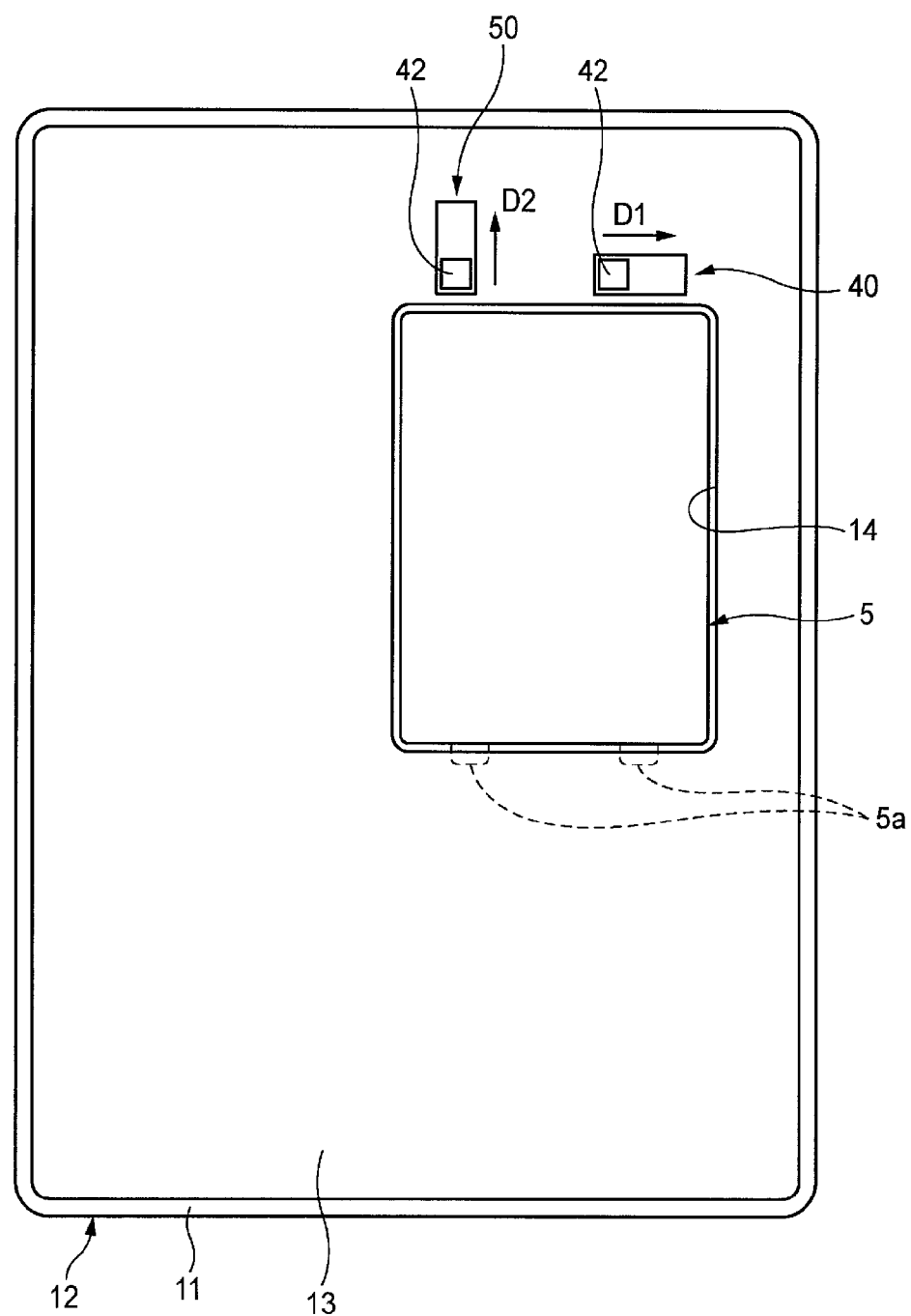
FIG. 15 is a view illustrating another example of placement of lock mechanisms and setting of lock-release directions in the radiological image detection apparatus of FIG. 1.

FIG. 15 illustrates another example of placement of lock mechanisms and setting of a lock-release direction.

In the example illustrated in FIG. 15, one lock mechanisms 40 as illustrated in FIG. 5 and one lock mechanism illustrated in FIG. 7 are used, and these lock mechanisms 40 and 50 are installed adjacently to a sidewall part opposite to the sidewall part of the battery accommodating part 14 to which the hook 5a of the battery 5 is coupled. Further, a lock-release direction of one lock mechanism 40 is set to a first direction D1 along the sidewall part, and a lock-release direction of the lock mechanism 50 is set to a second direction D2 approximately perpendicular to the sidewall part, that is, approximately perpendicular to the first direction.

In accordance with the X-ray image detection apparatus 1 configured as described above, in the case where, according to the sliding operation between the surface of another member such as, for example, the installation surface of the X-ray image detection apparatus and the outer surface of the back surface, the force is exerted to each of the manipulation parts 42 of the two lock mechanisms exposed to the outer surface of the back member 13, both directions of the force exerted to each of the manipulation parts 42 are the same, but the lock-release directions of the two lock mechanisms are different from each other. Therefore, the possibility that the two lock mechanisms will be simultaneously released may be reduced so that the fixing of the battery 5 may be ensured.

An angle between the first direction D1 and the second direction D2 may be 90 degrees (see, for example, FIG. 15) or more, and more preferably, 180 degrees (for example, see FIGS. 11 and 12). Through the above-mentioned configuration, according to the sliding operation between the installation surface at which the X-ray image detection apparatus 1 is installed and the outer surface of the back member 13, the possibility that the two lock mechanisms will be simultaneously released by the force having the same exertion direction and exerted to each of the manipulation parts 42 of two lock mechanisms exposed to the outer surface of the back member may be further reduced.

Although the examples in which the lock-release directions of two lock mechanisms are different are described above by way of examples, the number of lock mechanisms is not limited to two, but may be three or more. In this case, lock-release directions of these lock mechanisms need to include at least two different directions.

Figure 16:
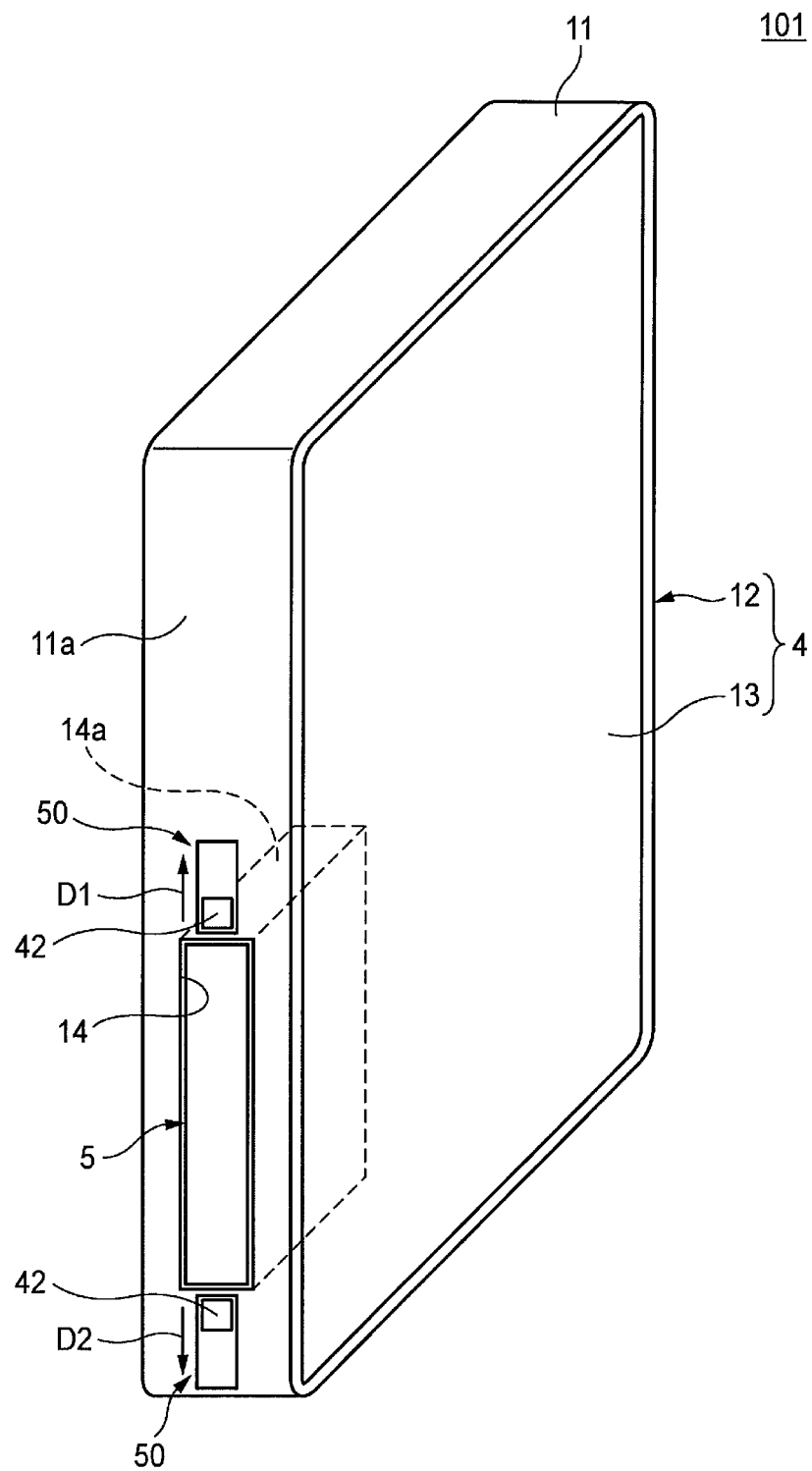
FIG. 16 is a perspective view illustrating a configuration of another example of a radiological image detection apparatus in accordance with another embodiment of the present invention.

FIG. 16 illustrates a configuration of a radiological image detection apparatus in accordance with another embodiment of the present invention. Meanwhile, the same reference numerals will be used to indicate the same components as those of the above-mentioned X-ray image detection apparatus 1, and a description thereof will be omitted The X-ray image detection apparatus 101 illustrated in FIG. 16, which is a so-called electronic cassette, includes a flat panel detector (FPD) 2, a case 4 accommodating a base 3, and a battery 5 supplying an operation power to the FPD 2.

A battery accommodating part 14 is installed at one sidewall part 11a of four sidewall parts 11 of a front member 12 configuring the case 4. In addition, two lock mechanisms are installed in a scheme in which the battery accommodating part 14 is sandwiched between the lock mechanisms in a length direction of the sidewall part 11a at which the battery accommodating part 14 is installed. As the lock mechanism, the lock mechanism 50 as illustrated in FIG. 7 of which the lock-release direction is a straight line direction approximately perpendicular to the sidewall part 14a of the battery accommodating part 14 to which the lock mechanism 50 is installed adjacently, may be used.

Further, a lock-release direction of one lock mechanism 50 is set to a first direction D1 along the sidewall part 11 of the front member 12 at which the battery accommodating part 14 is installed, and a lock-release direction of the other lock mechanism 50 is set to a second direction D2 opposite to the first direction D1.

In accordance with the X-ray image detection apparatus 101 configured as described above, when, according to the sliding operation between the surface of another member such as, for example, a jacket for carrying, a jacket for reinforcing, or a jacket for attaching a grid, and an outer surface of the sidewall part 11 of the front member 12 at which the battery accommodating part 14 is installed, the force is exerted to each of the manipulation parts 42 of the two lock mechanisms exposed to the outer surface of sidewall part 11, both directions of the force exerted to each of the manipulation parts 42 are the same, but lock-release directions of the two lock mechanisms are different from each other. Therefore, the possibility that the two lock mechanisms will be simultaneously released may be reduced, so that the fixing of the battery 5 may be ensured. In addition, as the battery is attached to the side, the performance of droplet-proof with respect to blood, or the like, may be improved.

The lock mechanism of the battery described above may be conveniently used particularly for a medical electronic cassette. Since the electronic cassette may perform a continuous photographing as compared to the cassette in accordance with the related art, a single electronic cassette is used to photograph not only a single patient as in the related art, but may be used to photograph a plurality of patients. Therefore, a single radiography room needs to include a single electronic cassette. However, there may be a case where the battery may not be used while being charged due to an exhaustion of power thereof. Therefore, it is generally considered that a plurality of batteries are prepared in a single electronic cassette, and when the power of the battery is exhausted, the photographing may be performed while sequentially exchanging the battery. In addition, the fact that the electronic cassette is a medical device and tends to be expensive as compared to general devices for a daily life is one of the reasons of exchanging to use a plurality of batteries with respect to a single electronic cassette. Therefore, on the assumption that batteries are frequently exchanged, the requirement for convenience in view of the operation such as a simple attachment and a detachment is significantly high. In addition, when the battery is faulted due to an error during the photographing, the photographing may be fault such that a patient may be unnecessarily exposed to X-rays. Therefore, it is important to prevent the battery from being faulted during the photographing. In consideration of these matters, when the lock mechanism in accordance with the present invention is installed, which may be easily attached and detached and unable to be detached by an error, the operation efficiency and safety of the photographing is improved, such that the convenience may be significantly improved.

Although the examples of using general X-rays as a radiation is described above, the present invention is not limited to the X-rays. For example, other radiations such as α-rays or γ-rays may also be used.

As set forth above, in the present specification, a radiological image detection apparatus described in the following (1) to (12) has been disclosed.

(1) A radiological image detection apparatus including: a radiological image sensor configured to detect radiation to generate image data; a case configured to accommodate the radiological image sensor therein; a battery accommodated in a battery accommodating part installed in the case and configured to supply an operation power to the radiological image sensor; and a lock mechanism configured to lock and fix the battery accommodated in the battery accommodating part, in which: the lock mechanism includes at least one first lock mechanism and at least one second lock mechanism, each including a coupling member moving between a coupling position at which the lock mechanism is coupled to the battery and a non-coupling position, the coupling member is installed with a manipulation part exposed to an outer surface of a portion of the case in which the battery accommodating part is installed, and the first lock mechanism sets a first direction of a movement direction of the corresponding coupling member from the coupling position to the non-coupling position and the second lock mechanism sets a second direction of a movement direction of the corresponding coupling member from the coupling position to the non-coupling position, being different from the first direction.

(2) The radiological image detection apparatus according to (1), in which an angle between the first and second directions is 90 degrees or more.

(3) The radiological image detection apparatus according to (1) or (2), in which at least one of the first and second lock mechanisms sets a straight line movement of the corresponding coupling member from the coupling position to the non-coupling position.

(4) The radiological image detection apparatus according to (1) or (2), in which at least one of the first and second lock mechanisms sets a rotational movement of the corresponding coupling member from the coupling position to the non-coupling position.

(5) The radiological image detection apparatus according to (1) or (2), in which the lock mechanism sets a combination of a straight line movement and a rotational movement of the corresponding coupling members from the coupling positions to the non-coupling positions.

(6) The radiological image detection apparatus according to any one of (1) to (5), in which each of the first and second lock mechanisms includes a pressing member configured to press the corresponding coupling member so that the coupling member moves from the non-coupling position to the coupling position.

(7) The radiological image detection apparatus according to any one of (1) to (6), further including: a base accommodated in the case and configured to support the radiological image sensor, in which the lock mechanism is supported by the base.

(8) The radiological image detection apparatus according to (7), in which the base has a rigidity higher than that of the portion of the case in which the battery accommodating part is installed.

(9) The radiological image detection apparatus according to (7), in which the lock mechanism is fixed to the base.

(10) The radiological image detection apparatus according to (9), in which the lock mechanism is fixed to the portion of the case in which the battery accommodating part is installed, and at least a region of the case to which the lock mechanism is fixed is supported by the base.

(11) The radiological image detection apparatus according to any one of (1) to (10), in which the battery accommodating part is formed in a bottom portion of the case so as to be concave, and a dimension of each of the first and second lock mechanisms in a depth direction of the battery accommodating part is equal to or smaller than a depth of the battery accommodating part.

(12) The radiological image detection apparatus according to any one of (1) to (11), in which the battery has a hook provided at an edge thereof, the hook being coupled to a sidewall part surrounding the battery accommodating part, and each of the first and second lock mechanisms locks an edge opposite to the edge of the battery at which the hook is installed to fix the battery.

What is claimed is:

1. A radiological image detection apparatus comprising:
a radiological image sensor configured to detect radiation to generate image data;
a case that accommodates the radiological image sensor therein;
a battery accommodated in a battery accommodating part installed in a bottom part of the case and that supplies an operation power to the radiological image sensor; and
lock mechanisms that lock and fix the battery accommodated in the battery accommodating part,
wherein each lock mechanism includes a coupling member which moves between a coupling position at which the lock mechanism is coupled to the battery and a non-coupling position, and a press member which presses the coupling member moving from the non-coupling position to the coupling position,
the coupling member is installed with a manipulation part being exposed by protruding from an outer surface of the bottom part of the case in which the battery accommodating part is installed, and
the lock mechanisms include at least one first lock mechanism in which a movement direction of the coupling member from the coupling position to the non-coupling position is set to a first direction, and at least one second lock mechanism in which a movement direction of the coupling member from the coupling position to the non-coupling position is set to a second direction, the second direction being different from the first direction.

2. The radiological image detection apparatus according to claim 1, wherein
an angle between the first and second directions is equal to or greater than 90 degrees.

3. The radiological image detection apparatus according to claim 1, wherein
the lock mechanisms include a lock mechanism in which a movement of the coupling member from the coupling position to the non-coupling position is a straight line movement.

4. The radiological image detection apparatus according to claim 1, wherein
the lock mechanisms include a lock mechanism in which a movement of the coupling member from the coupling position to the non-coupling position is a rotational movement.

5. The radiological image detection apparatus according to claim 1, wherein
the lock mechanisms include a lock mechanism in which a movement of the coupling member from the coupling position to the non-coupling position is a combination of a straight line movement and a rotational movement.

6. The radiological image detection apparatus according to claim 1, further comprising:
a base accommodated in the case and that supports the radiological image sensor,
wherein each lock mechanism is supported by the base.

7. The radiological image detection apparatus according to claim 6, wherein
the base has a rigidity higher than that of a portion of the case in which the battery accommodating part is installed.

8. The radiological image detection apparatus according to claim 6, wherein
each lock mechanism is fixed to the base.

9. The radiological image detection apparatus according to claim 8, wherein
each lock mechanism is fixed to a portion of the case in which the battery accommodating part is installed, and
at least a region of the portion of the case to which the lock mechanism is fixed is supported by the base.

10. The radiological image detection apparatus according to claim 1, wherein
the battery accommodating part is formed in the bottom part of the case so as to be concave, and
a dimension of the lock mechanism in a depth direction of the battery accommodating part is equal to or less than a depth of the battery accommodating part.

11. The radiological image detection apparatus according to claim 1, wherein
the battery has a hook provided at an edge thereof, the hook being coupled to a sidewall part surrounding the battery accommodating part, and
the lock mechanism locks and fixes an edge of the battery opposite to the edge of the battery at which the hook is provided.

* * * * *